US009232786B2

(12) United States Patent
Rodrigues et al.

(10) Patent No.: US 9,232,786 B2
(45) Date of Patent: Jan. 12, 2016

(54) DISPERSANTS FOR AGRICULTURAL APPLICATIONS

(75) Inventors: Klin A. Rodrigues, Signal Mountain, TN (US); Mark Alexander, Fort Worth, TX (US)

(73) Assignee: AKZO NOBEL CHEMICALS INTERNATIONAL B.V., Amersfoort (NL)

( * ) Notice: Subject to any disclaimer, the term of this patent is extended or adjusted under 35 U.S.C. 154(b) by 0 days.

(21) Appl. No.: 13/265,162

(22) PCT Filed: Apr. 19, 2010

(86) PCT No.: PCT/EP2010/055081
§ 371 (c)(1), (2), (4) Date: Oct. 19, 2011

(87) PCT Pub. No.: WO2010/121976
PCT Pub. Date: Oct. 28, 2010

(65) Prior Publication Data
US 2012/0040827 A1    Feb. 16, 2012

Related U.S. Application Data

(60) Provisional application No. 61/171,603, filed on Apr. 22, 2009.

(30) Foreign Application Priority Data

Jun. 3, 2009   (EP) ..................................... 09161815

(51) Int. Cl.
| A01N 25/14 | (2006.01) |
| A01N 25/10 | (2006.01) |
| A01N 25/04 | (2006.01) |
| A01N 25/30 | (2006.01) |
| C08F 220/06 | (2006.01) |
| C08F 220/18 | (2006.01) |
| C08F 220/56 | (2006.01) |

(52) U.S. Cl.
CPC ................ *A01N 25/10* (2013.01); *A01N 25/04* (2013.01); *A01N 25/14* (2013.01); *A01N 25/30* (2013.01); *C08F 220/06* (2013.01); *C08F 220/18* (2013.01)

(58) Field of Classification Search
None
See application file for complete search history.

(56) References Cited

U.S. PATENT DOCUMENTS

| 3,959,237 | A | * | 5/1976 | Blank ......................... 525/330.2 |
| 5,422,176 | A | | 6/1995 | Schuler et al. |
| 5,650,473 | A | | 7/1997 | Kimpton et al. |
| 5,693,716 | A | | 12/1997 | Bott et al. |
| 6,677,399 | B2 | | 1/2004 | Herbert et al. |
| 6,767,865 | B2 | | 7/2004 | Den Tandt et al. |
| 7,199,185 | B2 | | 4/2007 | Heming et al. |
| 2002/0007005 | A1 | | 1/2002 | Reck et al. |
| 2004/0197357 | A1 | | 10/2004 | Heming et al. |
| 2005/0148709 | A1 | | 7/2005 | Meyer et al. |
| 2005/0182219 | A1 | * | 8/2005 | Meyer et al. ................... 526/264 |
| 2008/0318785 | A1 | * | 12/2008 | Koltzenburg et al. ......... 504/139 |
| 2011/0166309 | A1 | | 7/2011 | Koltzenburg et al. |

FOREIGN PATENT DOCUMENTS

| CN | 101160047 A | 4/2008 |
| EP | 0 116 470 A1 | 8/1954 |
| EP | 0 562 344 A1 | 9/1993 |
| EP | 0 766 705 B1 | 4/1997 |
| EP | 0 862 856 B1 | 9/1998 |
| EP | 1 167 470 A1 | 1/2002 |
| RU | EA007354 B1 | 10/2006 |
| WO | WO 01/74941 A1 | 10/2001 |

OTHER PUBLICATIONS

European Serach Report for Application No. 09161815.7 completion date Oct. 8, 2009.
International Search Report for PCT Application No. PCT/EP2010/055081 dated Apr. 19, 2011.
International Preliminary Report for PCT Application No. PCT/EP2010/055081, mailed date Oct. 17, 2011.
Lowe et al., "Synthesis and Properties of Low-Polydispersity Poly(sulfopropylbetaine)s and their Block Copolymers," Macromolecules, vol. 32, pp. 2141-2148 (Apr. 6, 1999).
English Translation of Chinese Office Action dated Jun. 18, 2014.
Decision of Grant dated Feb. 24, 2015.
English translation of the Decision dated Feb. 24, 2015.

* cited by examiner

*Primary Examiner* — Tracy Vivlemore
*Assistant Examiner* — Monica Shin
(74) *Attorney, Agent, or Firm* — Norris McLaughlin & Marcus, P.A.

(57) ABSTRACT

An agrochemical formulation and its method of manufacture comprising an agrochemical active and a dispersant polymer comprising a copolymer of benzylmethacrylate, acrylic acid and 2-acrylamido-2-methyl propane sulfonic acid.

20 Claims, 1 Drawing Sheet

Pictures of 1% WDG dispersions in water after 24 hours. From left to right Polymer of Example 3, Comparative Example DS6 from US 6677399, Comparative Example DS10 from US 6677399 and Tersperse 2700.
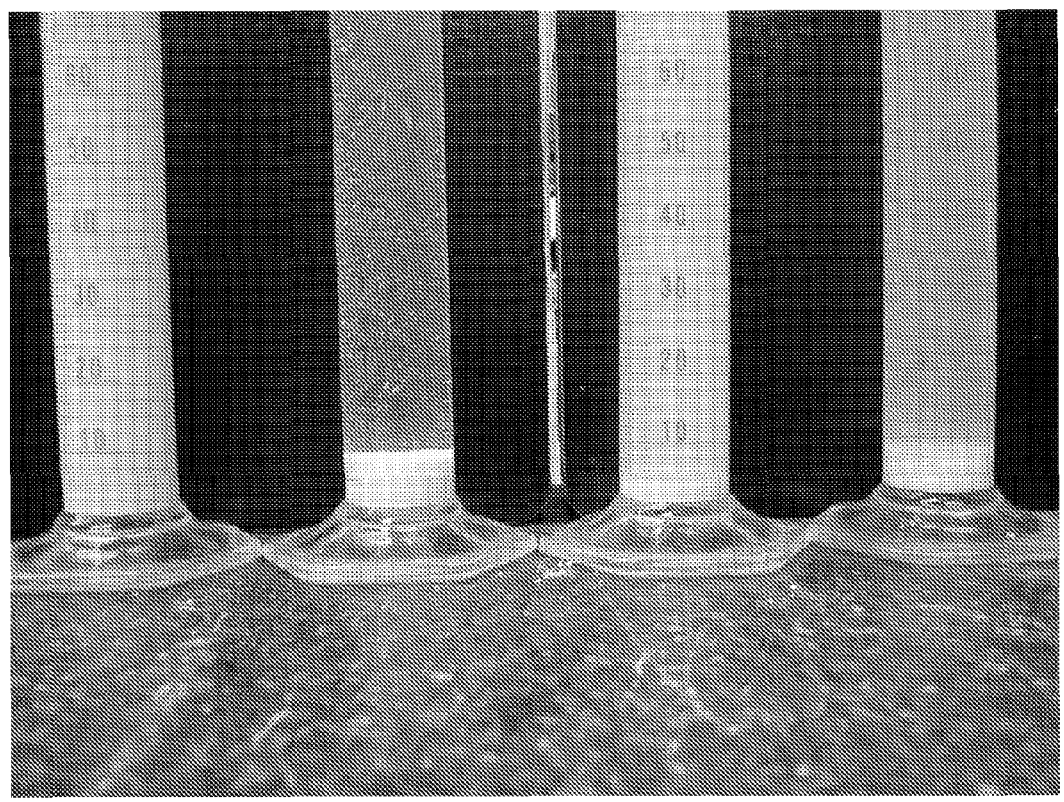

DISPERSANTS FOR AGRICULTURAL APPLICATIONS

CROSS-REFERENCES TO RELATED APPLICATIONS

This application is a National Stage entry of International Application PCT/EP2010/055081, filed Apr. 19, 2010, which claims the benefit of U.S. Patent Application No. 61/171,603, filed Apr. 22, 2009, and European Patent Application No. 09161815.7, filed Jun. 3, 2009. The contents of the aforementioned applications are incorporated herein by reference in their entireties.

BACKGROUND OF THE INVENTION

1. Field of the Invention

This invention relates to compositions used in agrochemical formulations, and, more particularly, to dispersants used in those compositions.

2. Prior Art

U.S. Pat. Nos. 6,677,399 and 6,767,865 describe the use of styrene based polymers in water dispersable granules and suspension concentrates.

EP 116470 describes the use of benzylmethacrylate copolymers with methacrylic acid in ink jet applications.

SUMMARY OF THE INVENTION

In a primary embodiment, the present invention comprises an agrochemical formulation comprising an agrochemical active and
a dispersant polymer of structure (I)

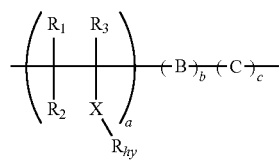
(I)

where $R_1$ $R_2$ and $R_3$ are independently H, $CH_3$, COOH and $CH_2COOH$ where X = linking group such as

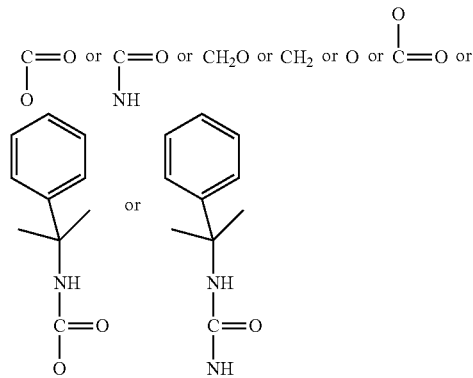

$R_{hy}$ is a hydrophobic moiety which is linear or branched alkyl, cycloalkyl, aryl, alkaryl or their alkoxylated derivative;

B is a moiety derived from polymerizing an olefinically unsaturated carboxylic acid monomer and its salts; and C is a moiety derived from polymerizing an olefinically unsaturated sulfonic acid monomer or phosphonic acid monomer and its salts, and is optional.

Other embodiments of the invention comprise details concerning the composition of the formulation, the polymer included in the formulation and a method of making the formulation, the details of which are hereinafter discussed.

DESCRIPTION OF THE DRAWING

FIG. 1 presents a photograph of graduated glass cylinders showing the extent of suspensibility of water dispersible granules dispersed in water corresponding to an embodiment of the invention and of granules of various comparative examples.

DETAILED DESCRIPTION OF THE INVENTION

The present invention regards compositions used in agrochemical formulations. As used herein, the term "agrochemical formulation" means any formulation that has applications in agricultural use.

The present invention is a composition containing an agrochemical active and a dispersant polymer of structure (I)

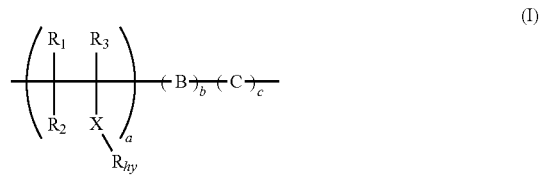
(I)

where $R_1$ $R_2$ and $R_3$ are independently H, $CH_3$, COOH and $CH_2COOH$ where X = linking group such as

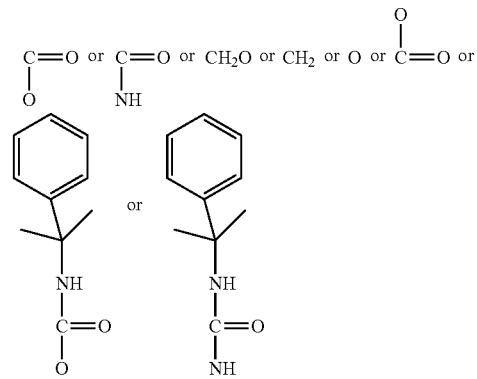

where $R_{hy}$ is a hydrophobic moiety which is linear or branched alkyl, cycloalkyl, aryl, alkaryl or their alkoxylated derivative. $R_{hy}$ is preferably aromatic and is naphthalene, ethoxylated naphthalene, phenyl, ethoxylated phenyl, benzyl or ethoxylated benzyl. The most preferred is phenyl or benzyl. However, $R_{hy}$ can be aliphatic or alkoxylated aliphatic such as a linear or branched $C_1$ to $C_{32}$ group. When $R_{hy}$ is linear aliphatic or alkoxylated linear aliphatic it is preferably methyl, ethyl or butyl or their ethoxylated derivatives. $R_{hy}$ is preferably branched aliphatic or alkoxylated branched aliphatic and is preferably 2-ethylhexyl, 2-butyloctyl, 2-hexyldecyl, 2-octyldodecyl, 2-decyltetradecyl, 2-dodecylhexadecyl, isopropyl, isobutyl, tertiary butyl, tertiary octyl or their ethoxylated derivatives. The most preferred is 2-ethylhexyl. If $R_{hy}$ is linear and greater than $C_8$ then unsaturated hydrophobes are preferred. These unsaturated hydrophobes can be oleyl, coco, soya, erucyl or tallow. The $R_{hy}$ can be incorporated into this dispersant polymer by polymerizing monomers such as but not limited to benzyl(meth)acrylate, phenyl(meth)acrylate, benzyl ethoxylate(meth)acrylate, phenyl ethoxylate (meth)acrylate, methyl methacrylate, methyl acrylate, 2-ethylhexyl (meth)acrylate, 2-butyloctyl (meth)acrylate, 2-hexyldecyl (meth)acrylate, 2-octyldodecyl (meth)acrylate, 2-decyltetradecyl (meth)acrylate, 2-dodecylhexadecyl (meth)acrylate, isopropyl (meth)acrylate, isobutyl (meth) acrylate, tertiary butyl (meth)acrylate, t-octyl acrylamide, octyl acrylate, lauryl acrylate, stearyl acrylate, behenyl acrylate, 2-ethylhexyl methacrylate, octyl methacrylate, lauryl methacrylate, stearyl methacrylate, behenyl methacrylate, 2-ethylhexyl acrylamide, octyl acrylamide, lauryl acrylamide, stearyl acrylamide, behenyl acrylamide, propyl acrylate, butyl acrylate, pentyl acrylate, hexyl acrylate, vinyl acetate, 1-allyl naphthalene, 2-allyl naphthalene, 1-vinyl naphthalene and 2-vinyl naphthalene.

B is a moiety derived from polymerizing an olefinically unsaturated carboxylic acid monomer and it salts and C is a moiety derived from polymerizing an olefinically unsaturated sulfonic acid monomer or phosphonic acid monomer and it salts and is optional. Useful olefinically unsaturated carboxylated monomers include but are not limited to acrylic acid, methacrylic acid, ethacrylic acid, α-chloro-acrylic acid, α-cyano acrylic acid, β-methyl-acrylic acid (crotonic acid), α-phenyl acrylic acid, β-acryloxy propionic acid, sorbic acid, α-chloro sorbic acid, angelic acid, cinnamic acid, p-chloro cinnamic acid, β-styryl acrylic acid (1-carboxy-4-phenyl butadiene-1,3), itaconic acid, maleic acid, citraconic acid, mesaconic acid, glutaconic acid, aconitic acid, fumaric acid, tricarboxy ethylene, muconic acid, 2-acryloxypropionic acid, and maleic acid. Moieties such as maleic anhydride or acrylamide that can be derivatized (hydrolyzed) to obtain a carboxylic acid moiety are also included. Combinations of olefinically unsaturated carboxylated monomers can also be used. In one aspect the anionic ethylenically unsaturated monomer is acrylic acid, maleic acid, methacrylic acid, 2-acrylamido-2-methyl propane sulfonic acid and its salts or mixtures thereof. The preferred salts are alkali metal salts such as sodium and potassium. However, the acidic groups in these polymers may be neutralized by amines such as ammonia, alkanol amines and aliphatic and aromatic amines. Preferred alkanol amines are mono, di and triethanolamine.

Examples of olefinically unsaturated sulfonic acid monomer or phosphonic acid monomers and their salts, include but not limited to 2-acrylamido-2-methyl propane sulfonic acid, sodium styrene sulfonate, sodium 1-allyloxy 2 hydroxy propane sulfonate, allyloxybenzene sulfonic acid, vinyl sulfonic acid, sodium methallyl sulfonate, sulfonated styrene, allyloxybenzene sulfonic acid, vinyl phosphonic acid and others. When sodium styrene sulfonate is used then $R_{hy}$ is preferably aromatic or alkoxylated aromatic.

The dispersant polymer of structure (I) can be prepared by processes known in the art such as disclosed in U.S. Pat. No. 5,650,473 the relevant parts of which are incorporated by reference. The dispersant polymer of structure (I) can be random, blocky or star shaped copolymers. The preferred architecture is random or blocky or mixtures thereof. The architecture of structure (I) is preferably not a graft copolymer because graft polymers typically have a lot of homopolymer formation of the grafted side chains which leads to a less effective polymeric dispersant.

The number average molecular weight of structure (I) is preferably less than 20,000, more preferably less than 10,000 and most preferably less than 5,000. The polymer is preferably a solution polymer and not an emulsion or dispersion polymer. Emulsion and dispersion polymers typically have much higher molecular weights than those disclosed above. As a result, they tend to be poorer disperants than the lower molecular weight solution polymers. The polymer is preferably water soluble. For purposes of this invention, the polymer is soluble in water at pH 7 and 25 C to at least 100 grams per liter, more preferably at least 10 grams per liter and most preferably at least 1 gram per liter.

In structure (I) a, b, and c are the mole percent of the individual groups so that a+b+c=100. The lower limit of a is 0.1, more preferably 2 and most preferably at 5 mole % of the polymer. The upper limit of a is 95, more preferably 50 and most preferably 20 mole % of the polymer. The lower limit of c is 0, more preferably 1 and most preferably at 2 mole % of the polymer. The upper limit of c is 15, more preferably 10 and most preferably 5 mole % of the polymer. The value of c can be 0 especially when $R_{hy}$ is a branched or unsaturated hydrophobe or when the linking group X contains a urea or urethane moiety.

As used herein, the term "agrochemical active" means any material that is used in agricultural applications. These include but are not limited to formulations include herbicides, insecticides, fungicides, biocides, molluscicides, algaicides, plant growth regulators, anthelmintics, rodenticides, nematocides, acaricides, amoebicides, protozoacides, crop safeners and adjuvants. Usually, the agrochemical active will be a water insoluble or immiscible material. "Water insoluble or immiscible material" is defined as any active material that has a solubility of less than 0.1 wt % in water. Specific examples of actives include:

Herbicides: including triazines such as Atrazine {6-chloro-N-ethyl-N'-(I-methylethyl)-1,3,5-triazine-2,4-diamine, and Prometryn {N,N'-bis(1-methylethyl)-6(methylthio)-1,3,5-triazine)-2,4-diamine}, substituted ureas such as Diuron {N'-(3,4-dichlorophenyl)-N,Ndimethylurea}, sulphonyl ureas such as metsulfuron-methyl {2-[[[[(4-methoxy-6-methyl-1,3,5triazin-2-yl) amino]carbonyl]amino]sulfonyl]benzoate}, triasulfuron {2-(2chloroethoxy)-N-[[(4-methoxy-6-methyl-1,3,5-triazin-2-yl) amino]carbonyl]benzenesulfonamide}, tribenuron-methyl {methyl 2-[[[[(4-methoxy-6-methyl-1,3,5triazin-2-yl)methylamino]carbonyl]amino]sulfonyl]benzoate} and chlorsulfuron {2-chloro-N-[[(4-methoxy-6-methyl-1,3,5triazin-2-yl)amino]carbonyl] benzenesulfonamide}, bis-carbamates such as Phenmedipham {3-[(methoxycarbonyl) amino]phenyl (3-methylphenyl)carbamate};

Fungicides: including thiocarbamates, particularly alkylenebis(dithiocarbamate)s, such as Maneb {[1,2ethanediylbis-[carbamodithiato](2-)]manganese} and Mancozeb {[[1,2-ethanediyl-bis[carbamodithiato]] (2-)]manganese mixture with [[1,2-ethanediylbis [carbamodithiato]](2-)]zinc}, strobilurins such as azoxystrobin {methyl (E)-2-[[6-(2-cyanophenoxy)-4pyrimidinyl]oxy]-a-(methoxymethylene) benzeneacetate} 60 and kresoxim-methyl {(E)-a-(methoxyimino)-2-[(2methylphenoxy)methyl] benzeneacetic acid methyl ester}, dicarboximides such as iprodione {3-(3,5 dichlorophenyl)Nisopropyl-2,4dioxo imidazolidine-1-carboxamide}; azoles such as propiconazole {1-[2-(2,4-dichloro-phenyl)-4-65 propyl-1,3-dioxolan-2-yl-methyl-1H-1,2,4-triazole}, and tebuconazole {(RS)-I-p-chlorophenyl-4,4-dimethyl-3-(1H1,2,4-triazole-1-ylmethyl)pentan-3-ol}; halophthalonitriles such as chiorothalonil {2,4,5,6-tetrachloro-1,3 dicyanobenzene}; and inorganic fungicides such as Copper hydroxide {Cu(OH)2};

Insecticides: including benzoyl ureas such as Difiubenzuron {N-[[(4-chlorophenyl)amino]carbonyl]-2,6-5difiuorobenzamide)}; and carbamates such as carbaryl {I-naphthyl methylcarbamate}; and Acaricides including: tetrazines such as Clofentezine {3,6-bis(2-chlorophenyl)-1,2,4,5-tetrazine}.

The agrochemical active may be water-soluble. Among water soluble active materials, non-selective herbicides, particularly N-(phosphono-methyl)glycine type herbicides such as glyphosate and sulphosate {respectively the iso-propylamino and trimethylsulphonium salts of N-phosphonomethyl glycine} and phosphinyl amino acids such as glufosinate {2-amino-4-(hydroxymethylphosphinyl)butanoic acid}, particularly as the ammonium salt. Such water soluble actives can be used as the sole active material in water dispersible granules, but more usually, they will be used in combination with water insoluble or immiscible active materials in multiactive formulations.

The agrochemical active in many agricultural applications usually are hydrophobic or water insoluble in character and are, by necessity, often administered as finely divided solids suspended in aqueous media. The majority of these agrochemical actives are manufactured and marketed in concentrated form, possibly with the addition of other insoluble inert fillers, which are then diluted prior to application. For example, the agrochemical active is typically available in the form of a suspension concentrate (SC), wettable powder (WP), suspension emulsion (SE) or water dispersible granule (WDG). However, due to the generally hydrophobic nature of the agrochemical active, the addition of a suitable dispersant is essential in order to achieve a homogenous dispersion with a minimum of mixing, such as may be achieved readily by hand or with minimal mechanical mixing. Often, this is an especially challenging task since the water used is extremely hard and may have upto 1000 ppm of hardness as calcium carbonate. This requires that the dispersant be hard water tolerant. Conventional dispersants do not perform under these tough conditions. Furthermore, once a homogenous dispersion is achieved, the resulting suspension must remain stable for a time sufficient, at least, to allow application by usual means such as spraying. Any settling, agglomeration or flocculation of the finely divided solid may lead to inconsistent and ineffective application as well as blockage of the spraying equipment. It is therefore necessary to provide a dispersant which provides easy and homogenous dispersion and results in a suspension which maintains its stability during the application of the aqueous dispersion, especially in hard water conditions.

In agrochemical applications, a wide variety of insoluble materials such as agrochemical actives are delivered in aqueous suspension. Active principals such as those used in WP, WDG, SE and SC formulations are generally insoluble at ambient temperatures. Water insoluble materials which may advantageously be used in WP, WDG, SE and SC formulations include herbicides, insecticides, fungicides, biocides, molluscicides, algaicides, plant growth regulators, anthelmintics, rodenticides, nematocides, acaricides, amoebicides, protozoacides, crop safeners and adjuvants. Examples of such agrochemical actives commonly granulated or made as powders in agriculture include: triazine herbicides such as simazine, atrazine, terbuthylazine, terbutryn, prometryn and ametryn, urea herbicides such as diuron and fluometron, sulphonyl urea herbicides such as chlorsulfuron, metsulfuron methyl, nicosulfuron and triasulfuron, sulphonanilide herbicides such as fiumetsulam, organophosphate insecticides such as azinphos methyl, chlorpyrifos, sulprofos and azamethiphos, carbamate insecticides such as aldicarb, bendiocarb, carbaryl and BPMC, synthetic pyrethroids such as bifenthrin, as well as various types of fungicides including dimethomorph, benomyl, carbendazim, mancozeb, triazoles such as hexaconazole and diniconazole, acaricides such as propargite. A list of such products can be drawn from the Pesticide Dictionary (contained in the Farm Chemicals Handbook) or the British Crop Protection Society: Pesticides Manual. In addition, some fertilizers and also water soluble active principles may use water dispersible formulations either by addition of inert carriers for convenience in handling or to aid in a controlled release formulation. A wide variety of other insoluble materials are used in agricultural applications including fillers and carriers, for example but not limited to, natural and synthetic silicates and silicate minerals, mineral oxides and hydroxides and also natural and synthetically derived organic materials. Such materials may be added as porous carriers, as moisture inhibition agents, to aid binding or agglomeration properties of a formulation or simply to fill a formulation to a convenient weight. Examples of such fillers may include natural silicates such as diatomacious earth, synthetic precipitated silicas, clays such as kaolin, attapulgites and bentonites, zeolites, titanium dioxide, iron oxides and hydroxides, aluminium oxides and hydroxides, or organic materials such as bagasse, charcoal, or synthetic organic polymers. These other insoluble materials may be readily dispersed in accordance with the present invention.

An additional agent conventionally used in combination with dispersants used in the above formulations is a surfactant wetting agent. The role of the wetting agent in the case of SC formulations is to aid removal of air from particle surfaces during manufacture and to aid dilution in water. In the case of WP formulations the role of the wetter may be to aid penetration of the solids into water, while in the case of WDG formulations it may aid penetration of the granules into water and aid disintegration of granules back to primary particle size. In some cases the dispersant may itself function as a suitable wetting agent while in others the dispersant may show an antagonistic effect on the wetter. The surfactant wetting agent can be an alkyl or alkaryl sulfonates such as alkylbenzene sulfonates, alpha olefin sulfonate and alkyl naphthalene sulfonates. These surfactant wetting agents can be alkyl sulfates where the hydrophobe can be a linear or branched alcohol, an example being sodium lauryl sulfate. They may also be ethoxylated or non-ethoxylated alkyl or alkyaryl carboxylates as well as alkyl or alkyaryl phosphate esters. The surfactant wetting agent can be an alkylpolysaccharide; di or mono alkyl sulfosuccinate derivatives; a non-ionic surfactant loaded onto an inert silicate carrier; and a non-ionic surfactant delivered in the form of a urea surfactant complex. The surfactant wetting agent could also include nonionic surfactants loaded onto a soluble organic or inorganic carrier or an anionic surfactant such as a sulfosuccinate that uses sodium benzoate as a carrier. The preferred wetting agents are alpha olefin sulfonates, alkyl naphthalene sulfonates, dialkyl sulphosuccinates and combinations thereof.

The step of dispersing the formulation in an aqueous medium may be achieved by any convenient means dependent on the nature of the formulation. It is desirable that the dispersion of the formulation in an aqueous solution may be conducted either by hand or with a minimum of mechanical agitation. Mechanical agitation may include stirring, mixing, blending and other similar processes.

The suspension of insoluble material in aqueous medium will be typically used for the treatment of a substrate such as plant or other agricultural medium. The application of the suspension onto the substrate may be achieved by any convenient means, including spraying, and the like. Granules are generally dispersed in water prior to being sprayed by the farmer. Farm sprays may be as a small back-pack handspray or a large boom spray or other convenient means. Aerial spraying is also sometimes used. Formulations of the present invention may also be applied to the substrate directly, prior to dispersion. The subsequent application of rain or other aqueous media is sufficient for the formulation of the suspension of particulate material.

The present invention is described with reference to WP, WDG, SE and SC formulations. In each case, formulations provide a stable aqueous dispersion of finely milled insoluble hydrophobic particles. The stability properties of the dispersion and hence the effectiveness of the dispersion can be measured by means of a suspensibility test as described by the CIPAC test MT 15.1, 161 and 168. In this test the volume fraction of suspended material is compared to that which has settled out due to gravity after 30 minutes. Typically suspensibility about 70% would be considered as an effective dispersant for WDG and WP formulations, while in excess of 90% would be expected for an SC formulation. A preferred measure for a WDG formulation is a suspensibility of 70% or greater in a system containing 1000 ppm water hardness as $CaCO_3$. Another measure of the stability of the dispersion is the degree to which particles remain non-aggregated. This may also be a property of the even distribution of the dispersant in the formulation. The degree to which particles may be aggregated is often measured by a wet sieve retention test as described in CIPAC test MT 59.3. In this test the dispersed solid is poured through a series of fine sieves and retained material is measured as a fraction of the total amount of dispersed material. Formation of such aggregates is a major problem observed in WDG formulations and to a lesser extent in WP formulations.

Generally WP formulations are produced by milling the agrochemical active either alone or in combination with fillers, dispersants and/or surfactant wetters to a suitable particle size, typically in the 5-15 um range. The milled material is then dry blended with a surfactant wetter, and/or dispersant if not already present or with additional dispersants and/or surfactant wetters to give a homogeneous composition. The powder formulation is assessed for wettability according to a method such as CIPAC MT 53.5.1 and suspensibility as per CIPAC MT 15.1. A formulation will desirably have a wettability of less than 1 minute and a suspensibility above 80%. Below 60% would generally be considered unacceptable. Results which might be commercially acceptable are either determined by the local registration authority or by the standards set by the formulators themselves.

In the case of WDG formulations a suitably milled active ingredient with or without other fillers, typically of particle size 5 to 15 um, may be mixed with one or more surfactant wetters and one or more dispersants. Typically an excess of water is added to bind the particles together into agglomerates. The excess water is later reduced by suitable air drying techniques to an optimal level. The agglomerates are typically granulated using one of many techniques including pan granulation, drum granulation, fluid bed granulation, spray drying, tableting or extrusion techniques which are well known to those skilled in the art. The wetter and dispersant may either be powder blended with the active ingredient or alternatively blended as an aqueous solution in the water used to aid agglomeration. The active ingredient, fillers, wetter and dispersant may also be milled together in one operation prior to addition of water.

For a WDG formulation to be acceptable an additional requirement is that the said granules should readily disperse in water back to the primary dispersed particle size within a short period. This property is known as dispersibility and in describing the current invention it is measured as the time taken for granules to disperse back to primary particle size in water under a standard degree of agitation. A dispersion time of less than one minute is desirable, 20 seconds is excellent and 2 minutes is poor. Desirably the granules should also have good suspensibility. Suspensibility is typically tested using CIPAC MT 15.1. Above 70% is a desirable result, less than 60% is generally regarded as undesirable. In many cases when testing granules a so-called maximum surface coverage result is often obtained. This is where the suspensibility results reach a maximum level then plateau. Adding more dispersant will not generally improve the result. This phenomenon is thought to be due to the particle size distribution of the material. Usually there are a given number of particles which are of such a size that they will settle regardless of type and concentration of dispersant. Desirably the granules should have low wet sieve retention. Wet sieve retention is typically tested using CIPAC MT 59.3. For the 150 um sieve less than 0.1% retained material is desirable. Less than 0.02% is more desirable. Likewise for the 53 um sieve less than 0.6% is desirable, anything less than this is more desirable.

A further desirable property of a WDG formulation is that the granules should be non-dusty and resistant to attrition. This is often a property of the method of granulation used and the level of compaction there obtained. Often there is an observed tradeoff between the dispersibility properties of a WDG formulation and the level of compaction and attrition resistance. Attrition resistance may be measured by subjecting granules to a set degree of agitation and measuring the level of smaller particles generated by means of passing through sieves of various sizes. Storage stability may be tested by storage at 50 degrees Celsius and tested as above at 1 month and 3 month intervals to determine if any properties have changed significantly.

As a further embodiment of the present invention in the case of WP and WDG formulations the dispersants herein described may be combined with surfactant wetting agents selected from the classes comprising alpha olefins sulfonate and their salts and alkyl naphthalene sulfonate and their salts, alkyl benzene sulfonates and their salts, alcohol sulfates and their salts, alkylpolysaccharides, nonionic surfactants loaded onto porous silicate carriers and urea surfactant complexes of non-ionic surfactants. The wetting agent may be combined in such formulations at a rate in excess of 1% w/w and preferably less than 5% w/w. The preferred wetting agents are alpha olefins sulfonate and their salts, alkyl naphthalene sulfonate and their salts, alkyl benzene sulfonates and their salts and alcohol sulfates and their salts. Examples of these include alpha olefins sulfonate and their salts such as Terwet 1004 from Huntsman and Witconate AOK from AkzoNobel Surface Chemistry with the most preferred being the sodium or potassium salts of $C_{14}$-$C_{16}$ alkane hydroxy and $C_{14}$-$C_{16}$ alkene sulfonates, alkyl naphthalene sulfonate and their salts such as Morwet DB from AkzoNobel Surface Chemistry or Agnique ANS 3DNP-R from Cognis. The most preferred being the butyl, dibutyl, isopropyl and diisopropyl naphthalene sulfonate salts. Examples of alkyl benzene sulfonates and their salts are Witconate 90 from AkzoNobel Surface Chemistry or Stepwet DF 90 from Stepan. The most preferred being the salts of the $C_{12}$ alkyl benzene sulfonate or $C_{10}$-$C_{16}$ alkyl benzene sulfonate. Examples of alcohol sulfates and their salts are Stepwet DF-95 from Stepan or Agnique SLS 1295P from Cognis. The most preferred being salts of lauryl or dodecyl alcohol sulfates.

In the case of SC formulations in the present invention an active ingredient is typically added to water containing a dispersant, preferably with a surfactant wetting agent together with a conventional non-ionic dispersant. A humectant may also be included. A dispersion is formed using high shear mixing. The dispersion is then milled by anyone of several means of wet milling so that the mean particle size of the dispersed solid is below 5 um more typically in the range of from 1 to 3 um. The resulting product is known as a millbase and may be modified with additives such as antifreeze, thickeners and antisettling agents, biocides and coloring agents may be added. For an SC formulation to be acceptable it should not show a high degree of thickening, settling or growth of aggregates over time. These physical properties can be assessed by visual observation. SC's generally require good viscosity and storage stability. Storage stability is usually assessed as degree of top settling or syneresis, sedimenting or "claying" which is the tendency to form a sticky layer on the bottom and "bleeding" which is the tendency of the dispersion to separate without necessarily displaying even settling. Redispersibility is also important. These may also be assessed visually.

Suspoemulsions (SE) consist of at least three phases: an aqueous phase, comprising an agrochemical active in solid dispersed form, and an organic phase comprising a second agrochemical active, either in liquid form or dissolved in an organic hydrophobic solvent. Normally the aqueous phase is the continuous phase. The second agrochemical active is typically water insoluble or immiscible. Liquid means that the active has a melting point of less than 30° C. The second agrochemical active which are liquid or soluble in a hydrophobic organic solvent, are acetanilide derivatives, as alachlor, metolachlor or S-metolachlor (S-enantiomer of racemic metolachlor); preferred are metolachlor and S-metolachlor. Suitable fungicides which can function as the second agrochemical active are for example benomyl, cyprodinil, dimethomorph, edifenphos, fenpropimorph, metalaxyl, (R)-metalaxyl (enantiomer). oxadixyl, pyrifenox, thiabendazol, tridemorph, azoxystrobin, kresoxim-methyl or triazoles such as propiconazol, difenoconazol, bromoconazol, cyproconazole, epoxyconazol, hexaconazol, ipconazol, fenbuconazol, myclobutanil, penconazol, tebuconazol, triadimefon, triadimenol, tetraconazol, triticonazol, or uniconazol; furtheron famoxadone, quinoxyfen, spiroxamin, fludioxonil, fenpiclonil, fenhexamid and 2-[a-{[(a-methyl-3-trifluoromethylbenzyl) imino]-oxy}-o-tolyl]-glyoxylic acid-methylester-O-methyloxim. Suitable hydrophobic organic solvents in which the pesticides may be dissolved are aliphatic and aromatic hydrocarbons such as hexane, cyclohexane, benzene, toluene, xylene, mineral oil or kerosin, mixtures or substituted naphthalenes, mixtures of mono- and polyalkylated aromatics, halogenated hydroarbons such as methylene chloride, chloroform and o-dichlorobenzene; phthalates, such as dibutyl phthalate or dioctyl phthalate; ethers and esters, such as ethylene glycol monomethyl or monoethyl ether, fatty acid esters; pyrrolinones, such as N-octylpyrrolidone, ketones, such as cyclohexanone; plant oils such as castor oil, soybean oil, cottonseed oil and possible methyl esters thereof; as well as epoxidised coconut oil or soybean oil.

EXAMPLE 1

An initial charge of 162 g of water and 188 g of isopropyl alcohol were added to a 2 liter glass reactor. The reactor contents were heated to reflux (approximately 84° C.). At reflux, continuous additions of a mixture of 127 g of acrylic acid, 174 g of benzyl methacrylate ($R_{hy}$ is aryl and benzyl), 0.6 g of dodecylmercaptan, 90.3 g of 2-acrylamido-2-methyl propane sulfonic acid sodium salt (50% solution) dissolved in 56 g of isopropyl alcohol were added over a period of 3 hours. A solution of 10.3 g of sodium persulfate dissolved in 115 g of water was simultaneously added but over a period of 3.5 hours. The reaction temperature was maintained at about 85-88° C. for one hour. The alcohol cosolvent was removed from the polymer solution by azeotropic distillation under vacuum. During the distillation, a mixture of 130 g of deionized water and 144 g of a 50 percent sodium hydroxide solution was added to the polymer solution. A small amount of ANTIFOAM 1400 (0.045 g) (from Dow Chemical) was added to suppress any foam generated during distillation. Approximately, 455 g of a mixture of water and isopropyl alcohol were distilled off. After distillation was completed, 135 g of water was added to the reaction mixture which was cooled to obtain a water white solution with 49.4% solids.

EXAMPLE 2

An initial charge of 162 g of water and 188 g of isopropyl alcohol were added to a 2 liter glass reactor. The reactor contents were heated to reflux (approximately 84° C.). At reflux, continuous additions of a mixture of 121.7 g of acrylic acid, 142.9 g of benzyl methacrylate, 0.7 g of dodecylmercaptan, 125 g of 2-acrylamido-2-methyl propane sulfonic acid sodium salt (50% solution) dissolved in 56 g of isopropyl alcohol were added over a period of 3 hours. A solution of 10.3 g of sodium persulfate dissolved in 115 g of water was simultaneously added but over a period of 3.5 hours. The reaction temperature was maintained at about 85-88° C. for one hour. The alcohol cosolvent was removed from the polymer solution by azeotropic distillation under vacuum. During the distillation, a mixture of 130 g of deionized water and 121.7 g of a 50 percent sodium hydroxide solution was added to the polymer solution. A small amount of ANTIFOAM 1400 (0.045 g) (from Dow Chemical) was added to suppress any foam generated during distillation. Approximately, 366 g of a mixture of water and isopropyl alcohol were distilled off. After distillation was completed, 235 g of water was added to the reaction mixture which was cooled to obtain a water white solution with 36.0% solids.

EXAMPLE 3

An initial charge of 162 g of water and 188 g of isopropyl alcohol were added to a 2 liter glass reactor. The reactor contents were heated to reflux (approximately 84° C.). At reflux, continuous additions of a mixture of 130.3 g of acrylic acid, 123.2 g of benzyl methacrylate, 0.6 g of dodecylmercaptan, 125 g of 2-acrylamido-2-methyl propane sulfonic acid sodium salt (50% solution) dissolved in 56 g of isopropyl alcohol were added over a period of 3 hours. A solution of 10.3 g of sodium persulfate dissolved in 115 g of water was simultaneously added but over a period of 3.5 hours. The reaction temperature was maintained at about 85-88° C. for one hour. The alcohol cosolvent was removed from the polymer solution by azeotropic distillation under vacuum. During the distillation, a mixture of 130 g of deionized water and 130.3 g of a 50 percent sodium hydroxide solution was added to the polymer solution. A small amount of ANTIFOAM 1400 (0.045 g) (from Dow Chemical) was added to suppress any foam generated during distillation. Approximately 366 g of a mixture of water and isopropyl alcohol were distilled off. After distillation was completed, 135 g of water was added to the reaction mixture which was cooled to obtain a water white solution with 38.5% solids.

EXAMPLE 4

An initial charge of 162 g of water and 188 g of isopropyl alcohol were added to a 2 liter glass reactor. The reactor contents were heated to reflux (approximately 84° C.). At reflux, continuous additions of a mixture of 139.7 g of acrylic acid, 98.6 g of benzyl methacrylate, 0.6 g of dodecylmercaptan, 125 g of 2-acrylamido-2-methyl propane sulfonic acid sodium salt (50% solution) dissolved in 56 g of isopropyl alcohol were added over a period of 3 hours. A solution of 10.3 g of sodium persulfate dissolved in 115 g of water was simultaneously added but over a period of 3.5 hours. The reaction temperature was maintained at about 85-88° C. for one hour. The alcohol cosolvent was removed from the polymer solution by azeotropic distillation under vacuum. During the distillation, a mixture of 130 g of deionized water and 140 g of a 50 percent sodium hydroxide solution was added to the polymer solution. A small amount of ANTIFOAM 1400 (0.045 g) (from Dow Chemical) was added to suppress any foam generated during distillation. Approximately, 375 g of a mixture of water and isopropyl alcohol were distilled off. After distillation was completed, 135 g of water was added to the reaction mixture which was cooled to obtain a water white solution with 40.0% solids.

EXAMPLE 5

A sample of sulfophenyl methallyl ether weighing 72 grams and 36.9 grams of sodium methallyl sulfonate was stirred into 390 grams of water and 133 grams of isopropanol in a 2 liter reaction vessel and heated to 85° C. A dilute solution containing 0.0083 grams of ferrous ammonium sulfate hexahydrate was added to the reactor. A monomer solution that consisted of a mixture of 200 grams of acrylic acid, 45.4 grams of methyl methacrylate ($R_{hy}$ is alkyl and methyl) and 16.4 grams of a 50% solution of 2-acrylamido-2-methyl propane sulfonic acid was added over a 3 hour period. 14.8 grams of sodium persulfate was dissolved in 69 grams of water and added to the reactor over a period of three hours and 30 minutes concurrent with the mixed monomer feed, except for the additional 30 minutes to react any residual monomer. The reaction mixture was held at 85° C. for 1 hour. A solution of 0.45 grams of erythorbic acid dissolved in 2.1 grams of water was then added. The reactor was set up for distillation and a mixture of isopropanol and water that weighed 225 grams was distilled off. The reaction product was then cooled and 200 grams of a 50% solution of sodium hydroxide was added. The final product was a clear yellow aqueous solution with approximately 40 percent solids.

EXAMPLE 6

Water dispersible Granules were produced using the polymers of this invention as well as those containing commercial products and comparative polymers from U.S. Pat. No. 6,677,399. For test purposes granules were prepared in 100 g lots. The weight of agrochemical active (Atrazine technical, 97% purity −92.8% w/w), polymeric dispersant (4.0% w/w), anionic and wetting agent (1.8% w/w) and Kaolin clay (1.4 wt % w/w) was added in an amount such that the total weight was 100 g. The Atrazine technical, polymeric dispersant, wetting agent and kaolin clay were blended together and milled using a horizontal hammer mill (Retsch model ZM1 with a 0.5 mm screen). After milling the samples were re-blended to ensure homogeneity. The feedstock was added to a small mixer where the required amount of water was added to achieve the consistency needed for extrusion. The paste was extruded using a Luwa Benchtop Granulator with a 1.2 mm screen. The extrudate was then dried.

Ageing:

The effect of ageing on the granules was assessed by storing the granules in an oven at 50° C. The disintegration or suspensibility of the granules was assessed fresh (0) and reassessed after storing the sample at 50° C. for 2 weeks. Ageing simulates what happens to the granules during storage. Good dispersants show a less than a 5% drop in suspensibility after ageing.

These granules were then tested for suspensibility using modified CITAC MT 168 method. Suspensibility is a measure for the stability of the dispersed solids in water. 1 g of the granular formulation was dispersed into 100 ml of 1000 ppm hardness water (1000 ppm hardness as $CaCO_3$ from Ricca Chemical Company) in a test cylinder, the cylinder was inverted 10 times and allowed to stand for 5 minutes, and the cylinder again inverted 10 times and allowed to stand for 30 minutes. The upper 90% were drawn off with a suction tube, taking care not to disturb the sediment. The remaining 10 mls of material was transferred quantitatively to a pre-weighed beaker, dried and re-weighed to determine the amount of material unsuspended. The % suspensibility was calculated using the following equation:

% Suspensibility=$111(1-a/w)$ a=dry mass of sample in the lower 10 mls of the suspension (g)

w=the mass of the sample taken

The dispersability was measured by number of inversions which was determined as follows: One gram of WDG was added to a graduated cylinder containing 250 mls of tap water. The WDG was allowed to wet completely before inverting the graduated cylinder. The graduated cylinder was stoppered, inverted 180°, enough time allotted to allow the WDG to travel the entire length of the graduated cylinder and the cylinder inverted another 180° revolution. Both revolutions were counted as a single inversion. The number of inversions needed to achieve a minimum of 95% dispersability was determined for the individual samples.

TABLE 1

Dispersancy and suspensibility data for a series of polymers in water dispersable granule applications using atrazine as the active ingredient.

| EXP number | % solids | % suspensibility at 1000 ppm water hardness as $CaCO_3$ in a WDG fresh (0) | % suspensibility at 1000 ppm water hardness as $CaCO_3$ in a WDG after aging at 50 C. for 2 weeks | Number of inversion | Description (Composition in mole percent) |
|---|---|---|---|---|---|
| DS1 | | 5.8 | 11.3 | 6 | Comparative Example from U.S. Pat. No. 6,677,399 |
| DS10 | | 69.2 | 43.5 | 5 | Comparative Example from U.S. Pat. No. 6,677,399 |
| Tersperse 2700 | | 12.7 | 32.7 | 9 | Commercially available from Huntsman |
| Gerapon T/36 | | 52.4 | 50.7 | 12 | Commercially available from Rhodia |
| Example 1 | 49 | 40.8 | | | 34% Benzylmethacrylate, 6% acrylamide-2-methylpropane sodium sulfonate, acrylic acid, Na salt |
| Example 2 | 36 | 84.5 | 62.8 | 6 | 29% Benzylmethacrylate 9.8% acrylamide-2-methylpropane sodium sulfonate, acrylic acid, Na salt |
| Example 3 | 38.5 | 89 | 83.1 | | 25% Benzylmethacrylate, 9.8% acrylamide-2-methylpropane sodium sulfonate, acrylic acid, Na salt |
| Example 4 | 40 | 84.5 | 77.8 | | 20% Benzylmethacrylate, 9.8% acrylamide-2-methylpropane sodium sulfonate, acrylic acid, Na salt |

Dispersants that give a percent suspensibility of 70 or greater on this test are considered to have excellent performance. In addition, if the number if inversions are less than 10, is an indication of good dispersability. The lower the number of inversions the better the dispersability. These data indicate that the polymers of this invention are superior to commercially available materials such as Tersperse 2700 (copolymer of styrene and Na methacrylate) and Gerapon T/36 (copolymer of isobutylene and maleic acid Na salt). In addition, the polymers of this invention are clearly superior dispersants when compared to the comparative polymers DS1 and DS10 of U.S. Pat. No. 6,677,399. Finally, the polymers of this invention have are far superior to those of U.S. Pat. No. 6,677,399 when the suspensibility is compared after ageing at 50 C.

EXAMPLE 7

Water dispersable granules were produced using Atrazine 90 as the active. The Atrazine 90WDG was diluted in 1000 ppm hardness water by adding 1 gram of WDG into 100 mls of water in a graduated cylinder. The graduated cylinders were inverted 15 times and allowed to sit undisturbed for 24 hours. The pictures of these cylinders are displayed in FIG. 1. These data indicate that the polymers of the invention show no settling of the active and are far superior to the polymers DS6 and DS10 of U.S. Pat. No. 6,677,399 as well as a commercially available material Tersperse 2700 all of which show significant amounts of settling.

EXAMPLE 8

Lower Molecular Weight Version of Example 4

An initial charge of 162 g of water and 188 g of isopropyl alcohol were added to a 2 liter glass reactor. The reactor contents were heated to reflux (approximately 84° C.). At reflux, continuous additions of a mixture of 139.7 g of acrylic acid, 98.6 g of benzyl methacrylate, 5.8 g of 3-mercaptopropionic acid, 125 g of 2-acrylamido-2-methyl propane sulfonic acid sodium salt (50% solution) dissolved in 56 g of isopropyl alcohol were added over a period of 3 hours. A solution of 15 g of sodium persulfate dissolved in 121 g of water was simultaneously added but over a period of 3.5 hours. The reaction temperature was maintained at about 85-88° C. for one hour. The alcohol cosolvent was removed from the polymer solution by azeotropic distillation under vacuum. During the distillation, a mixture of 130 g of deionized water and 140 g of a 50 percent sodium hydroxide solution was added to the polymer solution. A small amount of ANTIFOAM 1400 (0.045 g) (from Dow Chemical) was added to suppress any foam generated during distillation. Approximately, 375 g of a mixture of water and isopropyl alcohol were distilled off. After distillation was completed, 135 g of water was added to the reaction mixture which was cooled to obtain a water white solution with 39.0% solids.

EXAMPLE 9

Higher Molecular Weight Version of Example 4

An initial charge of 284 g of water and 66 g of isopropyl alcohol were added to a 2 liter glass reactor. The reactor contents were heated to reflux (approximately 84° C.). At reflux, continuous additions of a mixture of 139.7 g of acrylic acid, 98.6 g of benzyl methacrylate, 125 g of 2-acrylamido-2-methyl propane sulfonic acid sodium salt (50% solution) dissolved in 56 g of isopropyl alcohol were added over a period of 3 hours. A solution of 10.3 g of sodium persulfate dissolved in 115 g of water was simultaneously added but over a period of 3.5 hours. The reaction temperature was maintained at about 85-88° C. for one hour. The alcohol cosolvent was removed from the polymer solution by azeotropic distillation under vacuum. During the distillation, a mixture of 130 g of deionized water and 140 g of a 50 percent sodium hydroxide solution was added to the polymer solution. A small amount of ANTIFOAM 1400 (0.045 g) (from Dow Chemical) was added to suppress any foam generated during distillation. Approximately, 375 g of a mixture of water and isopropyl alcohol were distilled off. After distillation was completed, 185 g of water was added to the reaction mixture which was cooled to obtain a water white solution with 37.0% solids.

The molecular weights of these materials are listed in the Table 2 below:

| Sample | Example 4 | Example 8 | Example 9 |
|---|---|---|---|
| Weight molecular weight (Mw) | 6486 | 5021 | 9458 |
| Number average molecular weight (Mn) | 1804 | 1954 | 2974 |

EXAMPLE 10

To evaluate the effect of molecular weight, the dispersant polymers of Examples 4, 8 and 9 were tested for suspensibility using the procedure detailed in Example 6.

TABLE 3

Suspensibility data for a series of polymers with varying molecular weights.

| Sample number | % Suspensibility in 342 ppm water | % Suspensibility in 1000 ppm water |
|---|---|---|
| Example 4 | 87.5 | 85.0 |
| Example 8 | 94.9 | 92.2 |
| Example 9 | 83.1 | 82.4 |

These data in Table 3 indicate that the dispersancy performance of these samples of varying molecular weights are very good since the percent suspensibility numbers are all above 70%. In addition, all of these samples had good dispersability since all of them dissolved in 4 to 5 inversions.

EXAMPLE 10

A series of dispersants of this invention as well as commercial dispersants were screened with the Diuron 80WDG. The recipe used for screening was:
Diuron—82.5%
Dispersant—4.5%
Witconate AOK—2.0%
Kaolin clay—11.0%
Processing:
1. A WDG feedstock was made with all ingredients except for the dispersant.
2. The feedstock was blended, mechanically milled and re-blended.
3. The dry dispersants were added to aliquots of the feedstock, blended, mechanically milled and re-blended.
4. The feedstock was transformed into dough and extruded.
5. The extrudate was dried at 50° C. for three hours.

TABLE 4

Percent suspensibility for a series of dispersant polymers using Diuron as an active after ageing for 2 weeks at 50 C.

| | Gerapon T36 | Example 1 | Example 2 | Example 3 | Example 4 | Example 8 | Tersperse 2700 |
|---|---|---|---|---|---|---|---|
| % Suspensibility in 342 ppm water | 70.43 | 69.54 | 70.26 | 72.07 | 70.28 | 70.99 | 62.23 |
| % Suspensibility in 500 ppm water | 65.79 | 66.40 | 66.95 | 68.66 | 69.54 | 69.62 | 61.31 |
| % Suspensibility in 750 ppm water | 51.74 | 59.29 | 58.52 | 59.45 | 49.09 | 38.92 | 52.11 |
| % Suspensibility in 1000 ppm water | 23.23 | 32.82 | 29.71 | 20.80 | 21.53 | 23.00 | 14.05 |

These data indicate that the polymers of this invention are superior dispersants to commercially available materials.

EXAMPLE 11

Suspension concentrates were produced using the dispersants from Example 3 and DS4 from U.S. Pat. No. 6,767,865. The suspension concentrate was formulated using Atrazine as an active at 60% and 0.5 weight percent of the dispersant. The dispersant was weighed and added to the water and mixed until dissolved. The Atrazine was then added to the dispersant solution and mixed until completely dispersed using a high shear mixer.

The polymer from Example 3 formed a nice suspension concentrate with the viscosity profile measured by a Brookfield viscometer detailed in the Table 5 below.

| Polymer | Speed, RPMs | Viscosity, cps | Shear Stress |
| --- | --- | --- | --- |
| Example 3 | 5 | 76.8 | 5.07 |
| Example 3 | 10 | 76.8 | 10.2 |
| Example 3 | 20 | 85 | 22.5 |
| Example 3 | 30 | 96 | 37.9 |
| DS4 from U.S. Pat. No. 6,767,865 | | paste | |

In comparison, polymer DS4 from U.S. Pat. No. 6,767,865 did not form a usable suspension concentrate but formed a paste. Therefore, the polymers of this invention are clearly superior to these described in U.S. Pat. No. 6,767,865.

EXAMPLE 12

An initial charge of 202 g of water and 229 g of isopropyl alcohol were added to a 2 liter glass reactor. The reactor contents were heated to reflux (approximately 84° C.). At reflux, continuous additions of a mixture of 196 g of acrylic acid, 62.5 g of 2-ethylhexylacrylate, 0.73 grams of dodecylmercaptan, 152 g of 2-acrylamido-2-methyl propane sulfonic acid sodium salt (50% solution) dissolved in 68 g of isopropyl alcohol were added over a period of 3 hours. A solution of 12.6 g of sodium persulfate dissolved in 146 g of water was simultaneously added but over a period of 3.5 hours. The reaction temperature was maintained at about 85-88° C. for one hour. A small amount of ANTIFOAM 1400 (0.12 g) (from Dow Chemical) was added to suppress any foam generated during distillation. The alcohol cosolvent was removed from the polymer solution by azeotropic distillation. During the distillation, a mixture of 159 g of a 50 percent sodium hydroxide solution was added to the polymer solution followed by 300 grams of water/. Approximately, 480 g of a mixture of water and isopropyl alcohol were distilled off. After distillation was completed, 85 g of water and 1.2 grams if Proxel GXL was added to the reaction mixture which was cooled to obtain a clear pale yellow solution with 33.0% solids and a pH of 6.1.

EXAMPLE 13

An initial charge of 202 g of water and 229 g of isopropyl alcohol were added to a 2 liter glass reactor. The reactor contents were heated to reflux (approximately 84° C.). At reflux, continuous additions of a mixture of 183 g of acrylic acid, 93.7 g of 2-ethylhexylacrylate, 0.73 grams of dodecylmercaptan, 152 g of 2-acrylamido-2-methyl propane sulfonic acid sodium salt (50% solution) dissolved in 68 g of isopropyl alcohol were added over a period of 3 hours. A solution of 12.6 g of sodium persulfate dissolved in 146 g of water was simultaneously added but over a period of 3.5 hours. The reaction temperature was maintained at about 85-88° C. for one hour. A small amount of ANTIFOAM 1400 (0.12 g) (from Dow Chemical) was added to suppress any foam generated during distillation. The alcohol cosolvent was removed from the polymer solution by azeotropic distillation. During the distillation, a mixture of 159 g of a 50 percent sodium hydroxide solution was added to the polymer solution followed by 300 grams of water/. Approximately, 480 g of a mixture of water and isopropyl alcohol were distilled off. After distillation was completed, 85 g of water and 1.2 grams if Proxel GXL was added to the reaction mixture which was cooled to obtain a clear pale yellow solution with 32.6% solids and a pH of 6.4.

EXAMPLE 14

An initial charge of 202 g of water and 229 g of isopropyl alcohol were added to a 2 liter glass reactor. The reactor contents were heated to reflux (approximately 84° C.). At reflux, continuous additions of a mixture of 171.6 g of acrylic acid, 125 g of 2-ethylhexylacrylate, 0.73 grams of dodecylmercaptan, 152 g of 2-acrylamido-2-methyl propane sulfonic acid sodium salt (50% solution) dissolved in 68 g of isopropyl alcohol were added over a period of 3 hours. A solution of 12.6 g of sodium persulfate dissolved in 146 g of water was simultaneously added but over a period of 3.5 hours. The reaction temperature was maintained at about 85-88° C. for one hour. A small amount of ANTIFOAM 1400 (0.12 g) (from Dow Chemical) was added to suppress any foam generated during distillation. The alcohol cosolvent was removed from the polymer solution by azeotropic distillation. During the distillation, a mixture of 159 g of a 50 percent sodium hydroxide solution was added to the polymer solution followed by 300 grams of water/. Approximately, 480 g of a mixture of water and isopropyl alcohol were distilled off. After distillation was completed, 85 g of water and 1.2 grams if Proxel GXL was added to the reaction mixture which was cooled to obtain a clear pale yellow solution with 32.3% solids and a pH of 7.

EXAMPLE 15

Water dispersible Granules were produced using the polymers of Examples 12 and 14. For test purposes granules were prepared in 100 g lots. The weight of agrochemical active (Atrazine technical, 97% purity –92.8% w/w), polymeric dispersant (4.0% w/w), anionic and wetting agent (1.8% w/w) and Kaolin clay (1.4 wt % w/w) was added in an amount such that the total weight was 100 g. The Atrazine technical, polymeric dispersant, wetting agent and kaolin clay were blended together and milled using a horizontal hammer mill (Retsch model ZM1 with a 0.5 mm screen). After milling the samples were re-blended to ensure homogeneity. The feedstock was added to a small mixer where the required amount of water was added to achieve the consistency needed for extrusion. The paste was extruded using a Luwa Benchtop Granulator with a 1.2 mm screen. The wet extrudate was dried in a 50° C. oven to a constant weight. The suspensibility of the samples was then measured in a series of standard hard waters:

| | % suspensibility for Atrazine | |
|---|---|---|
| Water Hardness (ppm) | Example 12 | Example 14 |
| 342 | 83.2 | 79.1 |
| 500 | 81.2 | 75.0 |
| 1000 | 79.6 | 74.3 |

The composition of the Ametryn WDG is Ametryn technical, 95% purity –84.2% w/w, polymeric dispersant (6.0% w/w), anionic wetting (2.0% w/w), fumed silica (1.0% w/w) and kaolin clay (6.8% w/w).

The polymers of Example 12 and 14 were also tested for the agricultural active Ametryn.

| | % suspensibility for Ametryn | |
|---|---|---|
| Water Hardness (ppm) | Example 12 | Example 14 |
| 342 | 56.5 | 71.6 |
| 500 | 60 | 68.5 |
| 750 | 57.6 | 63.2 |
| 1000 | 53.3 | 64.8 |

The composition of the Diuron 80WDG is Diuron technical, 97% purity—82.5% w/w, polymeric dispersant (4.5% w/w), anionic wetting agent (2.0% w/w) and kaolin clay (11.0% w/w).

The polymers of Example 12 and 14 were also tested for the agricultural active Diuron.

| | % suspensibility for Diuron | |
|---|---|---|
| Water Hardness (ppm) | Example 12 | Example 14 |
| 342 | 64.4 | 74.1 |
| 500 | 62.8 | 71.9 |
| 750 | 63.1 | 69.2 |
| 1000 | 32.7 | 51.5 |

These data indicated that the polymers with the branched hydrophobes of this invention are excellent dispersing agents.

EXAMPLE 16

An initial charge of 202 g of water and 229 g of isopropyl alcohol were added to a 2 liter glass reactor. The reactor contents were heated to reflux (approximately 84° C.). At reflux, continuous additions of a mixture of 183 g of acrylic acid and 93.7 g of 2-ethylhexylacrylate, were added over a period of 3 hours. A solution of 12.6 g of sodium persulfate dissolved in 146 g of water was simultaneously added but over a period of 3.5 hours. The reaction temperature was maintained at about 85-88° C. for one hour. A small amount of ANTIFOAM 1400 (0.12 g) (from Dow Chemical) was added to suppress any foam generated during distillation. The alcohol cosolvent was removed from the polymer solution by azeotropic distillation. During the distillation, a mixture of 159 g of a 50 percent sodium hydroxide solution was added to the polymer solution followed by 300 grams of water. Approximately, 480 g of a mixture of water and isopropyl alcohol were distilled off. After distillation was completed, 85 g of water and 1.2 grams if Proxel GXL was added to the reaction mixture which was cooled to obtain a clear pale yellow solution.

The invention claimed is:

1. An agrochemical formulation comprising an agrochemical active and a water-soluble dispersant polymer of structure (I):

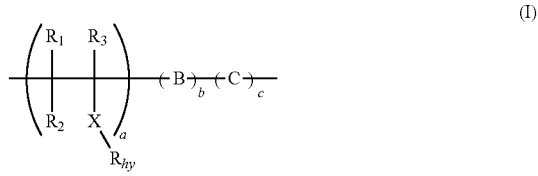

wherein
R$_1$ and R$_2$ both represent H;
R$_3$ represents H or CH$_3$;
X represents —C(O)O—;
R$_{hy}$ represents benzyl;
B represents a moiety derived from polymerizing acrylic acid or methacrylic acid or a salt thereof;
C represents a moiety derived from polymerizing 2-acrylamido-2-methylpropane sulfonic acid or a salt thereof;
a represents 0.1 to about 30 mole %;
c represents 0 to 5 mole %; and
a+b+c=100 mole %.

2. The agrochemical formulation of claim 1, wherein the formulation is in the form of a suspension concentrate (SC), suspension emulsion (SE), wettable powder (WP) or water dispersible granule (WDG).

3. The agrochemical formulation of claim 1, wherein said agrochemical active is selected from the group consisting of herbicides, insecticides, fungicides, biocides, molluscicides, algaicides, plant growth regulators, anthelmintics, rodenticides, nematocides, acaricides, amoebicides, protozoacides, crop safeners and adjuvants.

4. An agrochemical dispersant polymer comprising the polymer of structure (I):

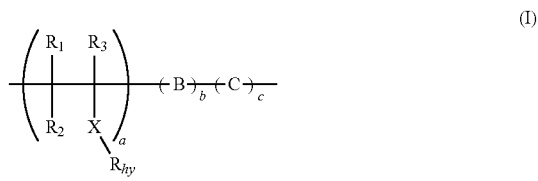

wherein
R$_1$ and R$_2$ both represent H;
R$_3$ represents H or CH$_3$;
X represents —C(O)O—;
R$_{hy}$ represents benzyl;
B represents a moiety derived from polymerizing acrylic acid or methacrylic acid or a salt thereof;
C represents a moiety derived from polymerizing 2-acrylamido-2-methylpropane sulfonic acid or a salt thereof;
a represents 0.1 to about 30 mole %;
c represents 0 to 5 mole %; and
a+b+c=100 mole %.

5. An agrochemical dispersant polymer according to claim 4, wherein the number average molecular weight of structure (I) is less than 20,000 Daltons.

6. An agrochemical formulation comprising an agrochemical active and a water-soluble dispersant polymer of structure (I):

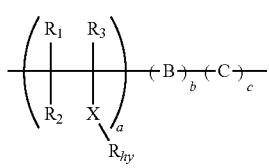

wherein
$R_1$ and $R_2$ both represent H;
$R_3$ represents H or $CH_3$;
X represents —C(O)O—;
$R_{hy}$ represents benzyl;
B represents a moiety derived from polymerizing acrylic acid or methacrylic acid or a salt thereof;
C represents a moiety derived from polymerizing 2-acrylamido-2-methylpropane sulfonic acid or a salt thereof;
a represents 0.1 to about 25 mole %;
c represents 0 to 10 mole %; and
a+b+c=100 mole %.

7. The agrochemical formulation of claim 6, wherein the formulation is in the form of a suspension concentrate (SC), suspension emulsion (SE), wettable powder (WP) or water dispersible granule (WDG).

8. The agrochemical formulation of claim 6, wherein said agrochemical active is selected from the group consisting of herbicides, insecticides, fungicides, biocides, molluscicides, algaicides, plant growth regulators, anthelmintics, rodenticides, nematocides, acaricides, amoebicides, protozoacides, crop safeners and adjuvants.

9. An agrochemical dispersant polymer comprising the polymer of structure (I):

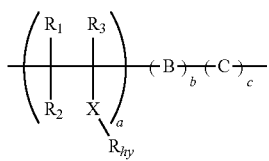

wherein
$R_1$ and $R_2$ both represent H;
$R_3$ represents H or $CH_3$;
X represents —C(O)O—;
$R_{hy}$ represents benzyl;
B represents a moiety derived from polymerizing acrylic acid or methacrylic acid or a salt thereof;
C represents a moiety derived from polymerizing 2-acrylamido-2-methylpropane sulfonic acid or a salt thereof;
a represents 0.1 to about 25 mole %;
c represents 0 to 10 mole %; and
a+b+c=100 mole %.

10. An agrochemical dispersant polymer according to claim 9, wherein the number average molecular weight of structure (I) is less than 20,000 Daltons.

11. An agrochemical formulation comprising an agrochemical active and a water-soluble dispersant polymer of structure (I):

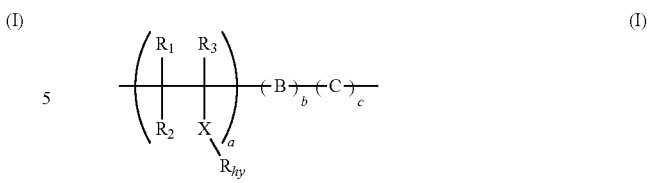

wherein
$R_1$ and $R_2$ both represent H;
$R_3$ represents H or $CH_3$;
X represents —C(O)O—;
$R_{hy}$ represents benzyl;
B represents a moiety derived from polymerizing acrylic acid or methacrylic acid or a salt thereof;
C represents a moiety derived from polymerizing 2-acrylamido-2-methylpropane sulfonic acid or a salt thereof; and
a+b+c=100 mole %;
wherein the agrochemical formulation exhibits a suspensibility in an aqueous medium of at least 70% after 30 minutes.

12. The agrochemical formulation according of claim 11, which is in the form of a water dispersible granule (WDG) and exhibits a suspensibility of 70% or greater in an aqueous medium containing 1000 ppm water hardness as $CaCO_3$.

13. A method of making the agrochemical formulation of claim 1, said method comprising the step of combining the agrochemical active and the dispersant polymer of structure (I).

14. A method of making an agrochemical formulation according to claim 13, further comprising the steps of:
milling the combination to a particle size range in order to obtain a stable, readily-suspendible aqueous dispersion; and
stabilizing the aqueous dispersion to obtain a suspension concentrate formulation suitable for dilution in water for agricultural use.

15. A method of making an agrochemical formulation according to claim 13, further comprising the step of:
milling the combination to a desired particle size to obtain a homogeneous wettable powder (WP) formulation.

16. A method of making an agrochemical formulation according to claim 13, further comprising the steps of:
agglomerating the combination to form discrete granular materials; and
drying the granular materials to obtain a water dispersible granule (WDG) formulation.

17. A method of making the agrochemical formulation of claim 6, said method comprising the step of combining the agrochemical active and the dispersant polymer of structure (I).

18. A method of making an agrochemical formulation according to claim 17, further comprising the steps of:
milling the combination to a particle size range in order to obtain a stable, readily-suspendible aqueous dispersion; and
stabilizing the aqueous dispersion to obtain a suspension concentrate formulation suitable for dilution in water for agricultural use.

19. A method of making an agrochemical formulation according to claim 17, further comprising the step of:
milling the combination to a desired particle size to obtain a homogeneous wettable powder (WP) formulation.

20. A method of making an agrochemical formulation according to claim 17, further comprising the steps of:

agglomerating the combination to form discrete granular materials; and drying the granular materials to obtain a water dispersible granule (WDG) formulation.

* * * * *